United States Patent
Lanver et al.

(10) Patent No.: US 8,692,025 B2
(45) Date of Patent: Apr. 8, 2014

(54) PROCESS FOR PREPARING M- OR P-SUBSTITUTED PHENYLALKANOLS BY ALKYLATION

(75) Inventors: Andreas Lanver, Mannheim (DE); Klaus Ebel, Lampertheim (DE); Karl Beck, Östringen (DE); Ralf Pelzer, Fürstenberg (DE); Jörg Botzem, Limburgerhof (DE); Ulrich Griesbach, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/503,515

(22) PCT Filed: Oct. 14, 2010

(86) PCT No.: PCT/EP2010/065466
§ 371 (c)(1),
(2), (4) Date: Apr. 23, 2012

(87) PCT Pub. No.: WO2011/048012
PCT Pub. Date: Apr. 28, 2011

(65) Prior Publication Data
US 2012/0209030 A1  Aug. 16, 2012

(30) Foreign Application Priority Data
Oct. 23, 2009 (EP) .................... 09173910

(51) Int. Cl.
*C07C 45/29* (2006.01)
*C07C 29/32* (2006.01)

(52) U.S. Cl.
USPC .......................................... 568/426; 568/715

(58) Field of Classification Search
USPC ................................ 568/426, 715
See application file for complete search history.

(56) References Cited

U.S. PATENT DOCUMENTS

2011/0118510 A1  5/2011  Weis et al.

FOREIGN PATENT DOCUMENTS

| DE | 2952719 A1 | 7/1981 |
|---|---|---|
| EP | 0045571 A1 | 2/1982 |
| JP | 2009830 A | 1/1990 |
| WO | WO-2008/053148 A1 | 5/2008 |
| WO | WO-2010/012675 A1 | 2/2010 |
| WO | WO-2011/048068 A2 | 4/2011 |

OTHER PUBLICATIONS

Ishii, et al., "Oxidative Coupling of Benzenes with αβ-Unsaturated Aldehydes by the Pd(OAc)$_2$/Molybdovanadophosphoric acid/O$_2$ System", J. Org. Chem., (2005), pp. 5471-5474.
International Search Report for PCT/EP2010/065466 mailed Feb. 14, 2011.

*Primary Examiner* — Sikarl Witherspoon
(74) *Attorney, Agent, or Firm* — Novak Druce Connolly Bove + Quigg LLP

(57) ABSTRACT

The invention relates to a process for the preparation of m- or p-substituted phenylalkanols of the formula (I)

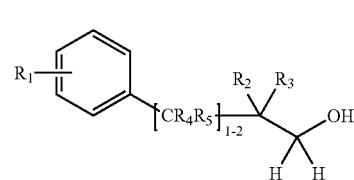

(I)

in which $R_1$ is bonded to the phenyl ring in the m- or p-position and is $C_1$-$C_5$-alkyl, and $R_2$, $R_3$, $R_4$ and $R_5$, independently of one another, are hydrogen or methyl, wherein an unsubstituted phenylalkanol of the formula (II)

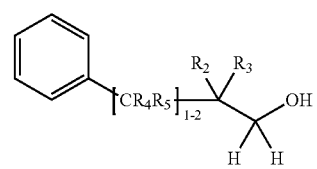

(II)

in which $R_2$, $R_3$, $R_4$ and $R_5$ have the meanings given under formula (I) is alkylated together with a $C_1$-$C_5$-alkyl halide of the formula (III)

$R_1$-Hal  (III), in which $R_1$ has the meaning given under formula (I) and Hal is halogen, in the presence of a Friedel-Crafts catalyst to give an m- or p-alkyl-substituted phenylalkanol of the formula (I), then the reaction mixture is worked-up and the desired m- or p-alkyl-substituted phenylalkanol of the formula (I) is separated off, the other formed by-products are returned to the reaction mixture and these are isomerized in the presence of a Friedel-Crafts catalyst to give the desired m- or p-alkyl-substituted phenylalkanol. From the m- or p-alkyl-substituted phenylalkanols of the formula (I), it is possible to form, by oxidation or dehydrogenation, as products of value, the corresponding aldehydes, which play an interesting role as fragrances and aroma chemicals.

15 Claims, No Drawings

PROCESS FOR PREPARING M- OR P-SUBSTITUTED PHENYLALKANOLS BY ALKYLATION

RELATED APPLICATIONS

This application is a national stage application (under 35 U.S.C. §371) of PCT/EP2010/065466, filed Oct. 14, 2010, which claims benefit of European Patent Application No. 09173910.2, filed Oct. 23, 2009.

The present invention relates to a process for the preparation of m- or p-alkyl-substituted phenylalkanols by Friedel-Crafts alkylation of phenylalkanols and subsequent isomerization of the undesired by-products to give the desired m- or p-alkyl-substituted phenylalkanol. The m- or p-alkyl-substituted phenylalkanols and also the m- or p-alkyl-substituted phenylalkanals prepared from these, for example derivatives of the odorant 3-phenyl-1-propanol, are of interest as aroma chemicals.

Various syntheses are known for preparing alkyl-substituted phenylalkanols and derivatives thereof.

WO 2008/053148 describes a 3-stage synthesis for preparing 3-(3-tert-butyl-phenyl)propanal starting from 1-tert-butyl-3-ethylbenzene. Here, the starting compound is firstly brominated to give 1-tert-butyl-3-(1-bromoethyl)benzene and then eliminated to give the correspondingly substituted stytrene. Hydroformylation then gives the 3-(3-tert-butylphenyl)propanal. This synthesis would not appear to be very suitable for an industrial process on account of low yields.

The preparation of 2-methyl-3-(3-tert-butylphenyl)propanal and of 2-methyl-3-(3-isobutylphenyl)propanal is achieved by Ishii et al. (J. Org. Chem. 2005, 70, 5471-5474) by palladium-catalyzed oxidative coupling of tert-butylbenzene or isopropylbenzene with methacrolein followed by a palladium-catalyzed hydrogenation. In the coupling step, a catalyst system consisting of $Pd(OAc)_2$ and $H_4PMo_{11}VO_{40} \times 26H_2O$ is used. A large amount of catalyst of ca. 7 mol % is required. At a yield of ca. 65%, the m/p ratio is 56/44 (for 2-methyl-3-(3-tert-butylphenyl)propanal) or 51/40 (for 2-methyl-3-(3-isobutylphenyl)propanal). This process too would not appear to be very suitable for an industrial process.

EP 0 045 571 describes the Friedel-Crafts alkylation of 2-methyl-3-phenylpropanol to 2-methyl-3-(3-tert-butylphenyl)propanol and 2-methyl-3-(4-tert-butylphenyl)propanol. The alkylating reagents used are isobutylene, diisobutylene and tert-butyl chloride. The catalysts used are iron chloride and phosphoric acid and the solvents used are methylene chloride or phosphoric acid. Depending on the reaction conditions and on the catalyst, m/p ratios of 1/13 to 1/5 are obtained. The overall yields (m-isomer and p-isomer) are up to 52%.

DE 29 52 719 likewise describes the iron chloride-catalyzed Friedel-Crafts alkylation of 2-methyl-3-phenylpropanol. In cyclohexane or dichloroethane solvent, a yield of 84-86% of 2-methyl-3-(4-tert-butylphenyl)propanol was obtained. The formation of the misomeric compound, (2-methyl-3-(3-tert-butylphenyl)propanol), was not demonstrated.

A disadvantage of the described Friedel-Crafts alkylations is the unidentified amount of the formed m-isomeric compound (m:p ratio is max. 1:5).

Compared with these known processes, the process according to the invention permits the m-substituted phenylalkanols or the p-substituted phenylalkanols, which serve as precursor for the very interesting correspondingly substituted phenylalkanals (phenyl-alkyl aldehydes), to be prepared cost-effectively in a very simple manner and in good yield.

The present invention relates to a process for the preparation of phenylalkanols substituted in the m- or p-position which can be obtained by Friedel-Crafts alkylation of unsubstituted phenylalkanols together with alkyl halides. The alkylation takes place over certain Friedel-Crafts catalysts. The invention therefore provides a process for the preparation of m- or p-alkyl-substituted phenylalkanols of the formula (I)

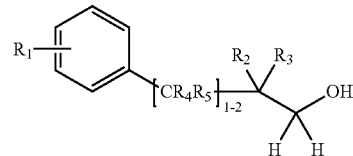

in which $R_1$ is bonded to the phenyl ring in the m- or p-position and is $C_1$-$C_5$-alkyl, and $R_2$, $R_3$, $R_4$ and $R_5$, independently of one another, are hydrogen or methyl, wherein an unsubstituted phenyl alkanol of the formula (II)

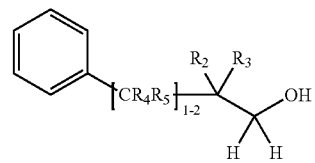

in which $R_2$, $R_3$, $R_4$ and $R_5$ have the meanings given below formula (I) is alkylated together with a $C_1$-$C_5$-alkyl halide of the formula (III)

$$R_1\text{-Hal} \qquad (III),$$

in which $R_1$ has the meaning given under formula (I) and Hal is halogen, in the presence of a Friedel-Crafts catalyst to give a mixture of m- and p-alkyl-substituted phenyl-alkanols of the formula (I), and then the reaction mixture, preferably in the presence of water at an alkaline pH, is worked-up, and the desired m-alkyl-substituted phenylalkanol of the formula (I) or the desired p-alkyl-substituted phenylalkanol of the formula (I) is separated off, preferably separated off by distillation, and the other formed by-products are returned to the reaction mixture and these are isomerized in the presence of a Friedel-Crafts catalyst to give the desired m- or p-alkyl-substituted phenylalkanol.

In order to influence the m- and p-ratio of the alkylation reaction in the desired direction, after the alkylation and after separating off the desired product, thus either of the m-alkyl-substituted phenylalkanol or of the p-alkyl-substituted phenylalkanol, an isomerization of the undesired components to the desired component also takes place. The reaction step characterized as isomerization refers to the adjustment of an equilibrium of the various components of the reaction under the conditions prevailing in the presence of a Friedel-Crafts catalyst. The isomerization step is followed by a work-up, preferably aqueous work-up, preferably at an alkaline pH, very particular preference being given to an aqueous work-up in the presence of alkali metal hydroxide solution, such as e.g. sodium hydroxide solution and/or potassium hydroxide solution, then the desired product is separated off, preferably separated off by distillation, and the undesired products are subjected again to an isomerization. The isomerization step can take place quasicontinuously by an aqueous work-up taking place after each isomerization step, preferably under alkaline conditions as stated above, with subsequent separation, preferably distillative separation, in order to increase the yield of the desired product.

The aqueous work-up of the reaction mass according to the present process takes place after the alkylation and also after the isomerization step by admixing the reaction mass at room temperature with water, preferably at an alkaline pH, particularly preferably in the presence of alkali metal hydroxide solution, in particular sodium hydroxide solution or potassium hydroxide solution. Afterwards, the desired reaction product is separated off, preferably by distillation.

It has been found that during the alkylation of unsubstituted phenylalkanols to alkyl-substituted phenylalkanols under certain conditions, m/p-isomer ratios of >1.5/1 can be obtained. Pure m- or p-substituted phenylalkanols of the formula (I) can scarcely be obtained in this way, and so the alkylation was followed by an isomerization of the undesired by-products to give one of the desired reaction products.

It is of course likewise possible to separate off the m-alkyl-substituted component and the p-alkyl-substituted component of the formula (I) e.g. by fractional distillation and to return the other by-products to the reaction mass in order to increase, through isomerization, the yield of both components.

Suitable $C_1$-$C_5$-alkyl halides in the process according to the invention are e.g.: methyl bromide, methyl iodide, ethyl bromide, ethyl iodide, n-propyl chloride, n-propyl bromide, n-propyl iodide, isopropyl chloride, isopropyl bromide, isopropyl iodide, n-butyl chloride, n-butyl bromide, isobutyl chloride, isobutyl bromide, sec-butyl chloride, sec-butyl bromide, tert-butyl chloride, tert-butyl bromide, n-pentyl chloride, n-pentyl bromide.

Preferred $C_1$-$C_5$-alkyl halides of the formula (III) are ethyl halide, in particular ethyl bromide and ethyl iodide, isopropyl halide, in particular isopropyl chloride and isopropyl bromide, isobutyl halide, in particular isobutyl chloride and isobutyl bromide, tert-butyl halide, in particular tert-butyl chloride.

Preference is given to a process for the preparation of m- or p-substituted phenylpropanols of the formula (IV)

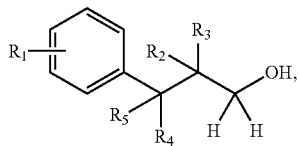

(IV)

in which $R_1$, $R_2$, $R_3$, $R_4$ and $R_5$ have the meanings given under formula (I) wherein an unsubstituted phenylpropanol of the formula (V)

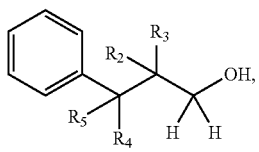

(V)

in which $R_2$, $R_3$, $R_4$ and $R_5$ have the meanings given under formula (IV) is alkylated together with a $C_1$-$C_5$-alkyl halide of the formula (III)

$R_1$-Hal (III), in which $R_1$ and Hal have the meanings given under formula (III), in the presence of a Friedel-Crafts catalyst to give a mixture of m- and p-alkyl-substituted phenylpropanol of the formula (IV), then the reaction mixture, preferably in the presence of water at an alkaline pH, is worked-up and the desired m- or p-alkyl-substituted phenylpropanol of the formula (IV) is separated off, preferably separated off by distillation, the other formed by-products are returned to the reaction mixture and these are isomerized in the presence of a Friedel-Crafts catalyst to give the desired m- or p-alkyl-substituted phenylpropanol.

Particular preference is given to a process wherein the starting compound is an unsubstituted phenylpropanol of the formula (VI)

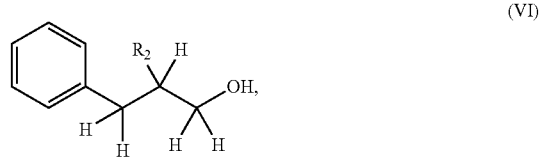

(VI)

in which $R_2$ has the meaning given under formula (I), this is reacted together with a $C_1$-$C_5$-alkyl halide of the formula (III)

$R_1$-Hal (III), in which $R_1$ and Hal have the meanings given under formula (III), in the presence of a Friedel-Crafts catalyst to give an m- or p-alkyl-substituted phenylpropanol of the formula (VII)

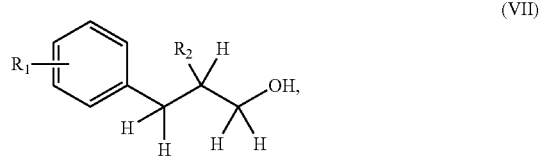

(VII)

in which $R_1$ and $R_2$ have the meaning given under formula (I), then the reaction mixture, preferably in the presence of water at an alkaline pH, is worked-up and the desired m- or p-alkyl-substituted phenylpropanol of the formula (VII) is separated off, preferably separated off by distillation, the other formed by-products are returned to the reaction mixture and these are isomerized in the presence of a Friedel-Crafts catalyst to give the desired m- or p-substituted phenylpropanol.

A very particularly preferred process is one in which, as starting compound, 2-methyl-3-phenylpropanol is reacted together with tert-butyl halide, in particular tert-butyl chloride, in the presence of aluminum trichloride ($AlCl_3$) to give 2-methyl-3-(3- or 4-tert-butylphenyl)propanol, then the reaction mixture, preferably in the presence of water at an alkaline pH, is worked-up and the desired 3-methyl-3-(3- or 4-tert-butylphenyl)-propanol is separated off, preferably separated off by distillation, and the other formed by-products are returned to the reaction mixture and these are isomerized in the presence of the Friedel-Crafts catalyst to give the desired 3-methyl-3-(3- or 4-tert-butylphenyl)propanol.

A likewise particularly preferred process is one in which the starting compound used is 2-methyl-3-phenylpropanol, 3-phenylpropanol, 3-phenyl-2,2-dimethylpropanol or 3-phenylbutanol, and the alkylation is carried out in the presence of an isobutyl halide, preferably isobutyl chloride, tert-butyl halide, preferably tert-butyl chloride, isopropyl halide, preferably isopropyl chloride, ethyl halide, preferably ethyl bromide, and in the presence of a Friedel-Crafts catalyst to give the compounds 2-methyl-3-(3- or 4-isobutylphenyl)propanol, 3-(3- or 4-tert-butylphenyl)propanol, 2-methyl-3-(3- or 4-isopropylphenyl)propanol, 3-(3- or 4-ethylphenyl)-2,2-dimethylpropanol or 3-(3- or 4-isopropylphenyl)butanol, and then the reaction mixture, preferably in the presence of water at an alkaline pH, is worked-up and the desired product is separated off, preferably separated off by distillation, and the other formed by-products are returned to the reaction mixture and isomerized in the presence of a Friedel-Crafts catalyst to give the desired product.

A further preferred embodiment is one in which, following work-up of the reaction mixture, preferably aqueous work-up at an alkaline pH, the desired m-substituted reaction product is separated off, i.e. preferably the m-alkyl-substituted phenylalkanol of the formula (I), or the m-alkyl-substituted phenylpropanol of the formula (IV), or the m-alkyl-substituted phenylpropanol of the formula (VII), or the 3-methyl-3-(3-tert-butyl-phenyl)propanol, is separated off or the compounds 2-methyl-3-(3-isobutylphenyl)-propanol, 3-(3-tert-butylphenyl)propanol, 2-methyl-3-(3-isopropylphenyl) propanol, 3-(3-ethylphenyl)-2,2-dimethylpropanol or 3-(3-isopropylphenyl)butanol are separated off.

Typical Friedel-Crafts catalysts can be used as catalysts. Examples which may be mentioned are $AlCl_3$, $AlBr_3$, $TiCl_4$, $ZrCl_4$, $VCl_3$, $ZnCl_2$, $FeBr_3$ and $FeCl_3$. Preference is given to using the Friedel-Crafts catalysts $AlCl_3$ or $AlBr_3$. In general, catalyst amounts of from 1 to 200 mol %, based on the molar amount of the phenylalkanol compound used, are used. Preference is given to catalyst amounts of from 33% to 110 mol %, based on the molar amount of the phenylalkanol compound used.

The alkylation and also the isomerization take place at temperatures between 0° C. and 100° C. Particular preference is given to temperatures between 10° C. and 50° C. The reaction times are 30 minutes to 24 hours. Particular preference is given to reaction times between 1 hour and 6 hours.

The alkylation reaction and also the isomerization reaction can be carried out solvent-free or in a solvent. Suitable solvents are: cyclohexane, toluene, p-tert-butyltoluene, dichloromethane, 1,2-dichloroethane, chlorobenzene, dichlorobenzene. Particular preference is given to dichloromethane and chlorobenzene.

Preferred starting materials for the alkylation are the following substrates: 2-methyl-3-phenylpropanol, 2-methyl-3-phenylpropanol, 3-phenylpropanol, 2-methyl-3-phenyl-propanol, 3-phenyl-2,2-dimethylpropanol, 3-phenylbutanol. Preferred alkylating agents are: isobutyl chloride, tert-butyl chloride, isopropyl chloride, ethyl bromide. These produce the following m-isomers as main products of the reaction: 2-methyl-3-(3-tert-butylphenyl)propanol, 2-methyl-3-(3-isobutylphenyl)propanol, 3-(3-tert-butyl-phenyl)propanol, 2-methyl-3-(3-isopropylphenyl)propanol, 3-(3-ethylphenyl)-2,2-dimethylpropanol, 3-(3-isopropylphenyl)butanol. The reaction also produces the following p-isomers as products of the reaction: 2-methyl-3-(4-tert-butylphenyl)propanol, 2-methyl-3-(4-isobutylphenyl)propanol, 3-(4-tert-butylphenyl)propanol, 2-methyl-3-(4-isopropylphenyl)propanol, 3-(4-ethylphenyl)-2,2-dimethylpropanol, 3-(4-isopropylphenyl)butanol. Particular preference is given to the substrates 2-methyl-3-(3- or 4-tert-butylphenyl)propanol.

The reaction is generally carried out in such a way that the catalyst is introduced together with the alkyl halide of the formula (III) into the phenylalkanol dissolved in the solvent. The work-up takes place by work-up with water and, optionally, sodium hydroxide solution, and also by distillation of the solvent. Purification of the crude product and isolation of the desired m- or p-substituted phenylalkanol generally takes place by distillation.

The phenylalkanols mono- and trisubstituted on the aromatic that are formed during the reaction and also the optionally undesired m- or p-alkyl-substituted phenylalkanol of the formulae (A), (B) and (C)

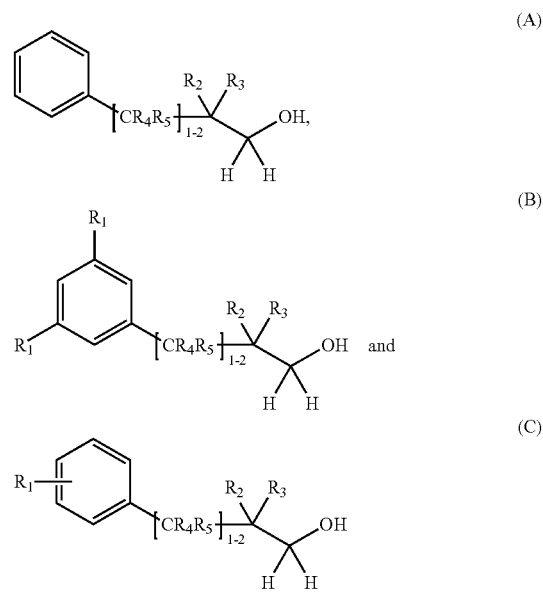

in which $R_1$, $R_2$, $R_3$, $R_4$ and $R_5$ have the meanings given under formula (I), are returned to the reaction mass after preferably aqueous work-up, preferably at an alkaline pH, and preferably distillative separation. As a result of returning these products to the reaction mass, the equilibrium between the p-substituted component and the m-substituted component and the mono- and tri-substituted phenylalkanols is freshly established time after time, as a result of which an increased fraction of the desired m- or p-substituted product is obtained since this desired product is removed from the reaction mass prior to each return (following work-up and distillation). Advantageously, the reaction takes place as a one-pot reaction in which, in a first step, the alkylation is carried out, the reaction product, together with unreacted starting material, following aqueous work-up, are separated off, preferably by distillation, the fraction of the desired m- or p-substituted phenylalkanol is collected and the by-products of the formulae (A), (B) and (C) are returned to the reaction vessel and, in a second step, are isomerized, again in the presence of a Friedel-Crafts catalyst, optionally in a solvent under the stated conditions, to give the desired m- or p-substituted phenylalkanol compound. The isomerization with subsequent aqueous work-up and distillative removal of the desired component and also the return of the other components of the formulae (A), (B) and (C) to the renewed isomerization can take place several times or quasicontinuously in order to obtain the fraction of the desired component, m- or p-alkyl-substituted phenyl-alkanol, in high yield.

The alkanols of the formula (I) prepared according to the invention can be converted to the corresponding aldehydes, based on dehydrogenation or oxidation methods known per se (cf. e.g.: Houben-Weyl "Methoden der organischen Chemie [Methods in organic chemistry]", Volume 7/1, p. 160ff, p. 171f). Particularly interesting compounds from this substance class are 2-methyl-3-(3- or 4-tert-butylphenyl)propanal, 2-methyl-3-(3- or 4-isobutylphenyl)propanal, 3-(3- or 4-tert-butylphenyl)propanal, 2-methyl-3-(3- or 4-isopropylphenyl)propanal, 3-(3- or 4-ethylphenyl)-2,2-dimethylpropanal and 3-(3- or 4-isopropylphenyl)butanal.

As described in EP-A-0 045 571, phenylpropanols can be converted to the corresponding phenylpropanals by oxidation or dehydrogenation. This reaction is achieved, for example, by copper chromite-catalyzed liquid-phase dehydrogenation.

Preferred starting materials for the reaction to give the aldehyde are 2-methyl-3-(3- or 4-tert-butylphenyl)propanol, 2-methyl-3-(3- or 4-isobutylphenyl)propanol, 3-(3- or 4-tert-butylphenyl)propanol, 2-methyl-3-(3- or 4-isopropylphenyl)propanol, 3-(3- or 4-ethylphenyl)-2,2-dimethylpropanol, 3-(3- or 4-isopropylphenyl)butanol. These produce the following aldehydes by oxidation or dehydrogenation: 2-methyl-3-(3- or 4-tert-butylphenyl)propanal, 2-methyl-3-(3- or 4-isobutylphenyl)propanal, 3-(3- or 4-tert-butylphenyl)propanal, 2-methyl-3-(3- or 4-isopropylphenyl)propanal, 3-(3- or 4-ethylphenyl)-2,2-dimethylpropanal, 3-(3- or 4-isopropylphenyl)butanal.

The invention thus further provides the preparation of the products of value of the formula (VIII), which play an interesting role as fragrances and aroma chemicals, obtainable from the m- or p-substituted phenylalkanols of the formula (I) by oxidation or dehydrogenation,

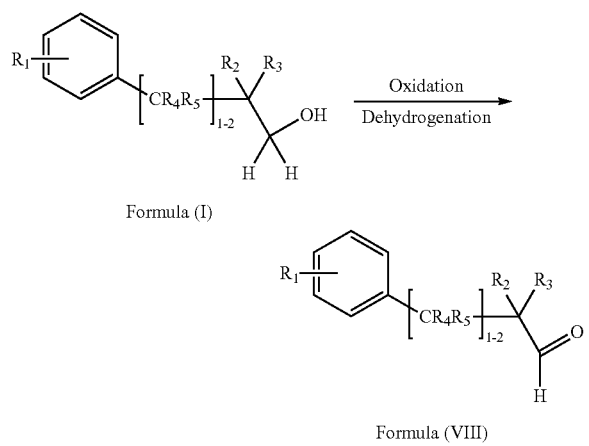

Formula (I)

Formula (VIII)

in which $R_1$, $R_2$, $R_3$, $R_4$ and $R_5$ have the meanings given under formula (I). The process according to the invention for the preparation of fragrances and aroma substances of the formula (VIII)

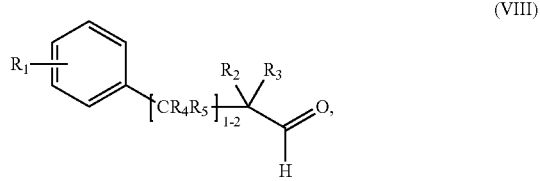
(VIII)

in which $R_1$ is bonded to the phenyl ring in the m- or p-position and is $C_1$-$C_5$-alkyl, and $R_2$, $R_3$, $R_4$ and $R_5$, independently of one another, are hydrogen or methyl, is notable for the fact that an unsubstituted phenylalkanol of the formula (II)

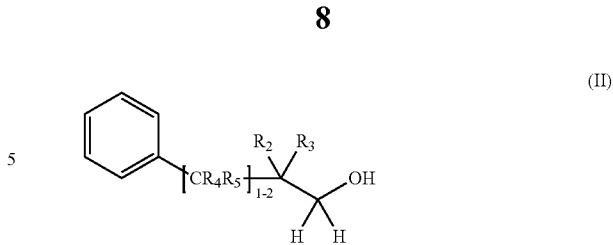
(II)

in which $R_2$, $R_3$, $R_4$ and $R_5$ have the meanings given under formula (VIII) is alkylated together with a $C_1$-$C_5$-alkyl halide of the formula (III)

$$R_1\text{-Hal} \tag{III}$$

in which $R_1$ and Hal have the meanings given under formula (III), in the presence of a Friedel-Crafts catalyst to give a mixture of m- and p-alkyl-substituted phenylalkanol of the formula (I)

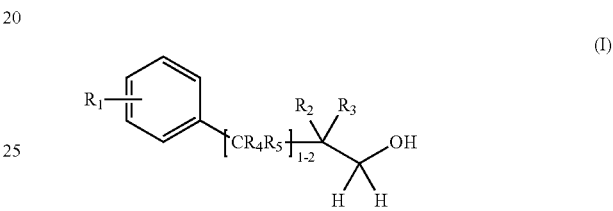
(I)

in which $R_1$, $R_2$, $R_3$, $R_4$ and $R_5$ have the meanings given under formula (I), then the reaction mixture, preferably in the presence of water at an alkaline pH, is worked-up, and the desired m- or p-alkyl-substituted phenylalkanol of the formula (I) is separated off, preferably separated off by distillation, and the other formed by-products are returned to the reaction mixture and these are isomerized in the presence of a Friedel-Crafts catalyst to give the desired m- or p-alkyl-substituted phenylalkanol, and then the resulting m- or p-alkyl-substituted phenylalkanol of the formula (I) is converted to the m- or p-alkyl-substituted phenylalkanal of the formula (VIII) by oxidation or dehydrogenation.

The invention is illustrated in more detail by the examples below. In the examples, all data in % are understood as meaning mol %.

EXAMPLES

Example 1

15.1 g (100 mmol) of 2-methyl-3-phenylpropanol were introduced as initial charge in 87 g of dichloromethane. Over the course of 4 hours, 13.4 g (100 mmol) of $AlCl_3$ and 9.3 g (100 mmol) of tert-butyl chloride were added at a temperature of 1-10° C. The mixture was heated to room temperature and worked-up with water and sodium hydroxide solution and the solvent was removed. This gave a mixture with the following composition: 2-methyl-3-(3-tert-butylphenyl)propanol (41%); 2-methyl-3-(4-tert-butylphenyl)propanol (24%); 3-(3,5-di-tert-butylphenyl)-2-methylpropanol (19%); 2-methyl-3-phenylpropanol (15%).

Example 2

15.1 g (100 mmol) of 2-methyl-3-phenylpropanol were introduced as initial charge in 78 g of dichloromethane. Over the course of 1.5 hours, 16.2 g (100 mmol) of $FeCl_3$ and 9.3 g (100 mmol) of tert-butyl chloride were added at a temperature of 1-5° C. The mixture was heated to room temperature and worked-up with water and sodium hydroxide solution and the solvent was removed. This gave a mixture with the following composition: 2-methyl-3-(3-tert-butylphenyl)propanol (36%); 2-methyl-3-(4-tert-butylphenyl)-propanol (24%); 3-(3,5-di-tert-butylphenyl)-2-methylpropanol (27%); 2-methyl-3-phenylpropanol (7.5%).

The invention claimed is:

1. A process for the preparation of m- or p-substituted phenylalkanols of the formula (I)

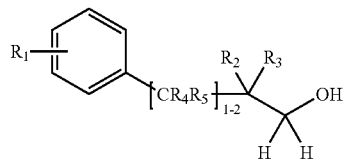
(I)

in which $R_1$ is bonded to the phenyl ring in the m- or p-position and is $C_1$-$C_5$-alkyl, and $R_2$, $R_3$, $R_4$ and $R_5$, independently of one another, are hydrogen or methyl, wherein an unsubstituted phenyl alkanol of the formula (II)

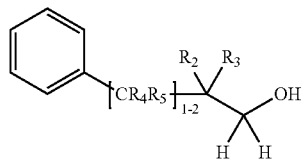
(II)

in which $R_2$, $R_3$, $R_4$ and $R_5$ have the meanings given below formula (I) is alkylated together with a $C_1$-$C_5$-alkyl halide of the formula (III)

$R_1$-Hal (III)

in which $R_1$ has the meaning given under formula (I) and Hal is halogen, in the presence of a Friedel-Crafts catalyst to give a mixture of m- and p-alkyl-substituted phenylalkanols of the formula (I), then the reaction mixture is worked-up, and the desired m-alkyl-substituted phenylalkanol of the formula (I) or the desired p-alkyl-substituted phenylalkanol of the formula (I) is separated off, the other formed products are returned to the reaction mixture and isomerized in the presence of a Friedel-Crafts catalyst to give the desired m- or p-alkyl-substituted phenylalkanol.

2. The process according to claim 1 for the preparation of m- or p-substituted phenylpropanols of the formula (IV)

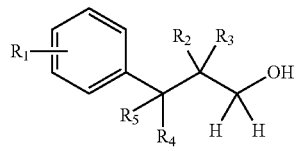
(IV)

in which $R_1$, $R_2$, $R_3$, $R_4$ and $R_5$ have the meanings given in claim 1, wherein an unsubstituted phenylpropanol of the formula (V)

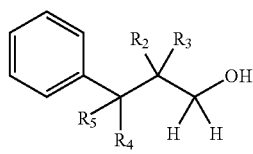
(V)

in which $R_2$, $R_3$, $R_4$ and $R_5$ have the meanings given under formula (IV) is alkylated together with a $C_1$-$C_5$-alkyl halide of the formula (III)

$R_1$-Hal (III)

in which $R_1$ and Hal have the meanings given in claim 1, in the presence of a Friedel-Crafts catalyst to give a mixture of m- and p-alkyl-substituted phenylpropanols of the formula (IV), and then the reaction mixture is worked-up and the desired m- or p-alkyl-substituted phenylpropanol of the formula (IV) is separated off, and the other formed by-products are returned to the reaction mixture and isomerized in the presence of a Friedel-Crafts catalyst to give the desired m- or p-alkyl-substituted phenylalkanol.

3. The process according to claim 1, wherein the starting compound used is an unsubstituted phenylpropanol of the formula (VI)

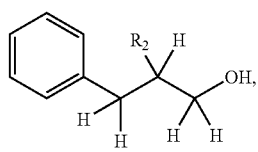
(VI)

in which $R_2$ has the meaning given in claim 1, this is reacted together with a $C_1$-$C_5$-alkyl halide of the formula (III)

$R_1$-Hal (III)

in which $R_1$ and Hal have the meanings given in claim 1, in the presence of a Friedel-Crafts catalyst to give an m- or p-alkyl-substituted phenylpropanol of the formula (VII)

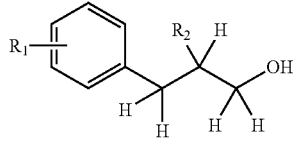
(VII)

in which $R_1$ and $R_2$ have the meanings given under formulae (VI) and (III), and then the reaction mixture is worked-up and the desired m- or p-alkyl-substituted phenylpropanol of the formula (VII) is separated off, and the other formed by-products are returned to the reaction mixture and these are isomerized in the presence of a Friedel-Crafts catalyst to give the desired m- or p-alkyl-substituted phenylpropanol.

4. The process according to claim 1, wherein the $C_1$$C_5$-alkyl halide used is ethyl halide, in particlar ethyl bromide and ethyl iodide, isopropyl halide, in particular isopropyl chloride and isopropyl bromide, isobutyl halide, in particular isobutyl chloride and isobutyl bromide, or tert-butyl halide, in particular tert-butyl chloride.

5. The process according to claim 1, wherein the Friedel-Crafts catalyst used is $AlCl_3$, $AlBr_3$, $TiCl_4$, $ZrCl_4$, $VCl_3$, $ZnCl_2$, $FeBr_3$, $FeCl_3$.

6. The process according to claim 5, wherein the Friedel-Crafts catalyst used is $AlCl_3$ or $AlBr_3$.

7. The process according to claim 1, wherein the Friedel-Crafts catalyst is used in an amount of from 1 to 200 mol %, in particular between 33 and 110 mol %, based on the molar amount of the phenylalkanol used.

8. The process according to claim 1, wherein the alkylation is carried out at a temperature between 0 and 100° C.

9. The process according to claim 1, wherein 2-methyl-3-phenyl-propanol is reacted together with tert-butyl halide, in particular tert-butyl chloride, in the presence of a Friedel-Crafts catalyst, in particular in the presence of aluminum trichloride or aluminum tribromide, to give 2-methyl-3-(3- or 4-tert-butylphenyl)propanol, and then the reaction mixture is worked-up and the desired 2-methyl-3-(3- or 4-tert-butylphenyl) propanol is separated off, and the other formed by-products are returned to the reaction mixture and these are isomerized in the presence of a Friedel-Crafts catalyst to give the desired 2-methyl-3-(3- or 4-tert-butylphenyl)propanol.

10. The process according to claim 1, wherein, following work-up of the reaction mixture, the desired m-substituted reaction product is separated off.

11. A process for the preparation of fragrances of the formula (VIII)

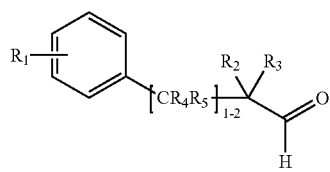

(VIII)

in which $R_1$ is bonded to the phenyl ring in the m- or p-position and is $C_1$-$C_5$-alkyl, and $R_2$, $R_3$, $R_4$ and $R_5$, independently of one another, are hydrogen or methyl, wherein an unsubstituted phenylalkanol of the formula (II)

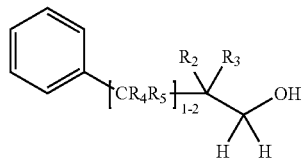

(II)

in which $R_2$, $R_3$, $R_4$ and $R_5$ have the meanings given under formula (VIII) is alkylated together with a $C_1$-$C_5$-alkyl halide of the formula (III)

$R_1$-Hal  (III)

in which $R_1$ has the meaning given under formula (VIII) and Hal is halogen, in the presence of a Friedel-Crafts catalyst to give an m- or p-alkyl-substituted phenylalkanol of the formula (I)

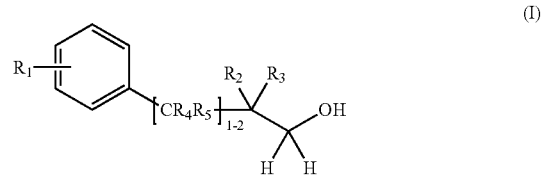

(I)

in which $R_1$, $R_2$, $R_3$, $R_4$ and $R_5$ have the meanings given under formula (VIII), and then the reaction mixture is worked-up and the resulting m- of p-alkyl-substituted phenylalkanol of the formula (I) is separated off, and the other formed by-products are returned to the reaction mixture and these are isomerized in the presence of a Friedel-Crafts catalyst to give the desired m- or p-alkyl-substituted phenylalkanol, and then converted to the m- or p-alkyl-substituted phenylalkanal of the formula (VIII) by oxidation or dehydrogenation.

12. The process according to claim 2, wherein the desired m- or p-alkyl-substituted phenylpropanol of the formula (IV) is separated off by distillation.

13. The process according to claim 3, wherein the desired m- or p-alkyl-substituted phenylpropanol of the formula (VII) is separated off by distillation.

14. The process according to claim 9, wherein the desired 2-methyl-3-(3- or 4-tert- butylphenyl)propanol is separated off by distillation.

15. The process according to claim 11, wherein the resulting m- of p-alkyl-substituted phenylalkanol of the formula (I) is separated off by distillation.

* * * * *